(12) United States Patent
Weiner

(10) Patent No.: US 6,505,075 B1
(45) Date of Patent: Jan. 7, 2003

(54) PERIPHERAL NERVE STIMULATION METHOD

(76) Inventor: Richard L. Weiner, 5950 Lindenshire La., #408, Dallas, TX (US) 75230

( * ) Notice: Subject to any disclaimer, the term of this patent is extended or adjusted under 35 U.S.C. 154(b) by 0 days.

(21) Appl. No.: 09/577,258

(22) Filed: May 22, 2000

Related U.S. Application Data

(60) Provisional application No. 60/136,690, filed on May 29, 1999.

(51) Int. Cl.$^7$ ................................................. A61N 1/18
(52) U.S. Cl. ......................................................... 607/46
(58) Field of Search ........................... 607/46, 117, 118; 600/26, 27

(56) References Cited

U.S. PATENT DOCUMENTS

| | | | | |
|---|---|---|---|---|
| 4,233,986 A | * | 11/1980 | Tannenbaum | ................ 607/46 |
| 4,586,509 A | * | 5/1986 | Liss et al. | ..................... 607/46 |
| 4,612,934 A | * | 9/1986 | Borkan | ......................... 607/62 |
| 5,938,690 A | * | 8/1999 | Law et al. | ..................... 607/46 |
| 6,104,957 A | * | 8/2000 | Alo et al. | ..................... 607/46 |

OTHER PUBLICATIONS

Weiner et al., "Peripheral Neurostimulation for Control for Intractable Occipital Neuralgia," Departments of Neurosurgery and Anesthesiology, Presbyterian Hospital of Dallas, TX, vol. 3, No. 3, Jul. 1999, pp 217–221.

Kuhn et al., "Occipital Neuralgias: Clinical Recognition of a Complicated Headache. A case Series and Literature Review," Journal of Orafacial Pain, vol. 11, No. 2, 1997.

Stechison et al., "Surgical Treatment of Greater Occipital Neuralgia: an Appraisal of Strategies," Acta Neurochirugia 1992; 131: 236–240.

Sulfaro et al., "Occipital Neuralgia Manifesting as Orofacial Pain," The University of Michigan School for Dentistry, vol. 80, No. 6, Dec. 1995.

* cited by examiner

*Primary Examiner*—George R. Evanisko
(74) *Attorney, Agent, or Firm*—Banner & Witcoff, Ltd.

(57) ABSTRACT

A method for treating pain by subcutaneous electrical stimulation of a peripheral nerve is disclosed. A lead is placed subcutaneously over a peripheral nerve that is causing pain. The peripheral nerve is electrically stimulated to cause paresthesia. The method encompasses subcutaneous placement of an electrical lead near any peripheral nerve causing pain and subsequent electrical stimulation of the nerve to cause paresthesia. In particular, a method for treating intractable occipital neuralgia using percutaneous peripheral nerve electrostimulation techniques is disclosed.

48 Claims, 10 Drawing Sheets

PERIPHERAL NERVE STIMULATION METHOD

This application claims benefit of Provisional Application 60/136,690 filed May. 29, 1999.

BACKGROUND OF THE INVENTION

1. Field of the Invention

This invention relates to a method for subcutaneously electrically stimulating peripheral nerves and in a particular embodiment relates to a method for subcutaneously electrically stimulating one or more occipital peripheral nerve to treat occipital neuralgia.

2. Description of Related Art

Peripheral nerves are nerves in the body other than the nerves of the brain or spinal cord. Peripheral nerve injury may result in the development of chronic intractable pain. Some patients prove unresponsive to conservative pain management techniques. Peripheral Nerve Stimulation (PNS) has developed as a successful therapy for pain management when the pain is known to result from a specific nerve. PNS is based in part on the Melzack-Wall gate control theory of pain. Sweet and Wespic first used electrical stimulation of peripheral nerves in the 1960s to mask the sensation of pain with a tingling sensation (paresthesia) caused by the electrical stimulation. Subsequent refinements in the technology, surgical technique and patient selection have led to improved long term results.

PNS is an accepted alternative for those patients who have failed more conservative pain management therapies. Clinical experience has shown that when applied to appropriate patients by trained practitioners, PNS can reduce pain, reduce narcotic intake to manage pain and improve the patient's activity levels and their quality of life. PNS has been recognized to have the following desirable characteristics:

The surgical procedure is relatively simple.

PNS is nondestructive. No known permanent surgical or chemical interruption of nerve pathways occurs.

PNS is reversible. If the patient does not benefit, the device can be turned off or removed. There are no known long-lasting medical or surgical side effects.

Patients can be tested for response prior to implant of the complete system.

Occipital nerves 2, 4 and 6 (FIG. 1) are peripheral nerves that exit the spinal cord at the C2 level of the cervical vertebrae and extend upward generally along the back and back-sides of the head. The lesser occipital nerve 2 extends upward and toward the sides of the head. The greater occipital nerve 4 extends upward toward the top of the head. The third occipital nerve 6 extends from near the neck around the back of the head toward the ear. Because of the location where the occipital nerves leave the spinal cord, the occipital nerves pass from the spinal column through muscle and fascia to the scalp.

Occipital neuralgia is a condition characterized by paroxysms of pain occurring within the distribution of the greater and/or lesser occipital nerves. Occipital neuralgia has been described as a "jabbing" pain in the area of the greater or lesser occipital nerve. The pain may radiate from the back or sides of the head toward the top or front of the head. Patients will vary in their reporting of this pain. It has been characterized in the medical literature as a unilateral or bilateral throbbing pain that frequently radiates to the forehead and to the frontal region (Stechison and Mullin, 1992) or as a lancinating pain extending from the suboccipital region up to the top of the head. The pain is less often described as including or consisting of a dull aching" (Sulfaro and Gobetti, 1995). Occipital neuralgia is often accompanied by diminished sensation and sometimes extreme localized tenderness over the applicable nerve.

Though known causes of occipital neuralgia include closed head injury, direct occipital nerve trauma, neuroma formation or upper cervical root compression (spondylosis or ligamentous hypertrophy), most patients have no demonstrable lesion. An anesthetic block of the greater occipital nerve can be used to confirm the diagnosis of occipital neuralgia (Khun, et al., 1997).

Traditional treatment options for intractable occipital nerve pain that has proven to be resistant to medications usually involve chemical, thermal or surgical ablation procedures following diagnostic local anesthetic blockade. Surgical approaches include neurolysis or nerve sectioning of either the occipital nerve in the occipital scalp or at the upper cervical dorsal root exit zone (extradural). Forammal decompression of C2 roots as well as C2 ganglionectomy have also been effective in reported cases.

Many patients with occipital neuralgia do not favorably respond to these medical treatments. Therefore, there is a need for an additional effective treatment of occipital neuralgia.

SUMMARY OF THE INVENTION

A method for treating pain by subcutaneous electrical stimulation is disclosed. A lead is placed subcutaneously over (superior to) a peripheral nerve that is causing pain The nerve is electrically stimulated to cause paresthesia. As a result, the pain is masked. The method of the invention encompasses subcutaneous placement of an electrical lead near any peripheral nerve causing pain and subsequent electrical stimulation of the nerve to cause paresthesia.

In particular, a method for treating intractable occipital neuralgia using percutaneous peripheral nerve electrostimulation techniques is disclosed. The method involves a subcutaneous electrode placement at the level of C1 transversely across the base of the occipital nerve trunk and subsequent electrical stimulation of the occipital nerve trunk. This stimulation produces paresthesia and pain relief covering the regions of occipital nerve pain It is therefore an object of the invention to provide a method for subcutaneously electrically stimulating nerves causing pain to create paresthesia.

It is another object of the invention to provide a method for percutaneously placing leads subcutaneously to create paresthesia.

These and other object of the invention will be clear from the following detailed description of the invention.

DETAILED DESCRIPTION OF THE INVENTION

Figure 1:
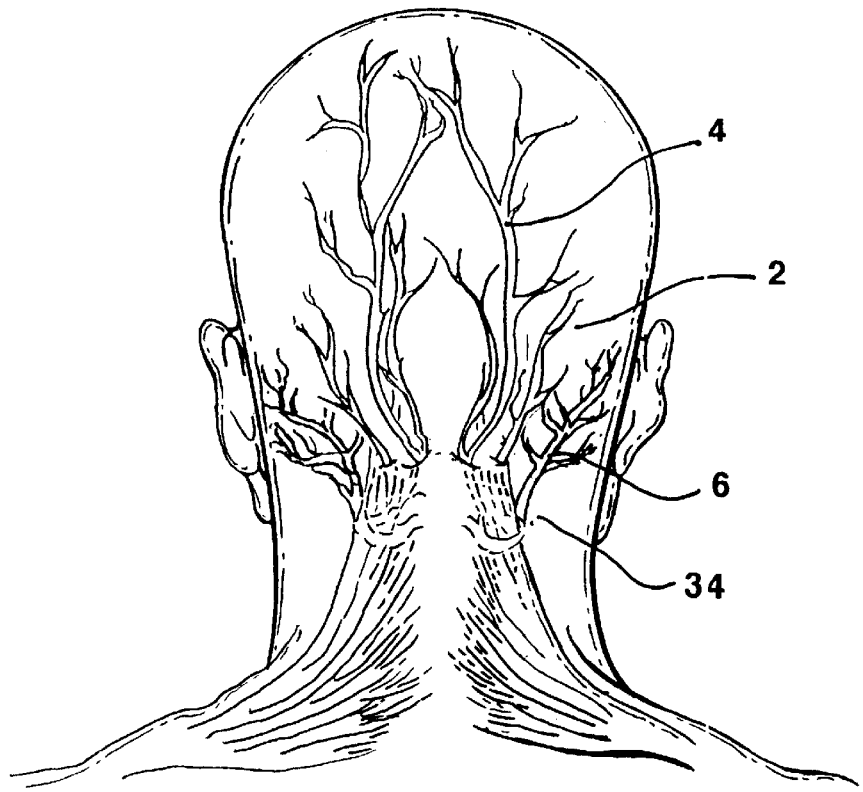
FIG. 1 is a schematic view of the occipital nerves.
Figure 2:
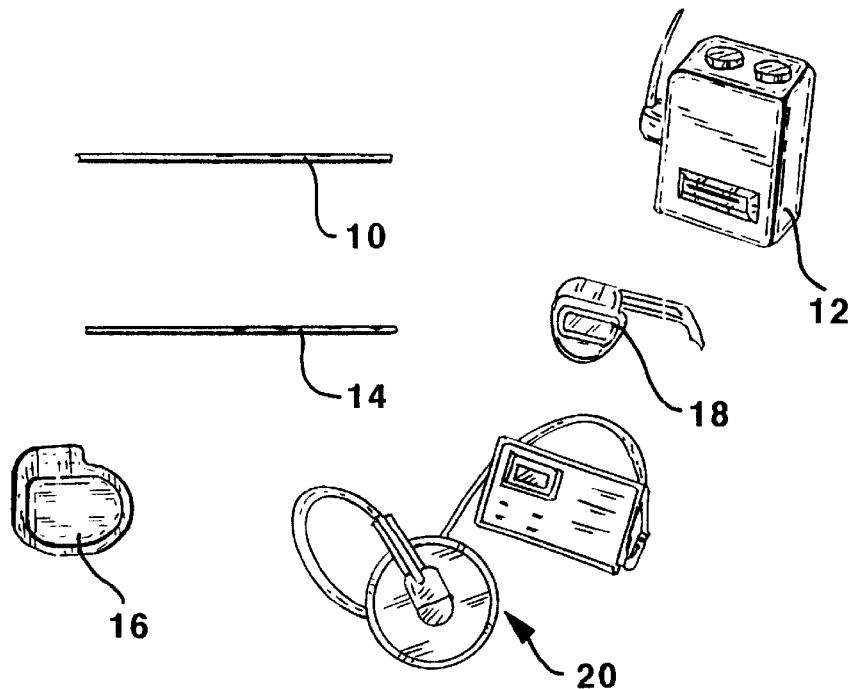
FIG. 2 is a schematic view of the hardware used to practice the invention of the present invention.
Figure 3:
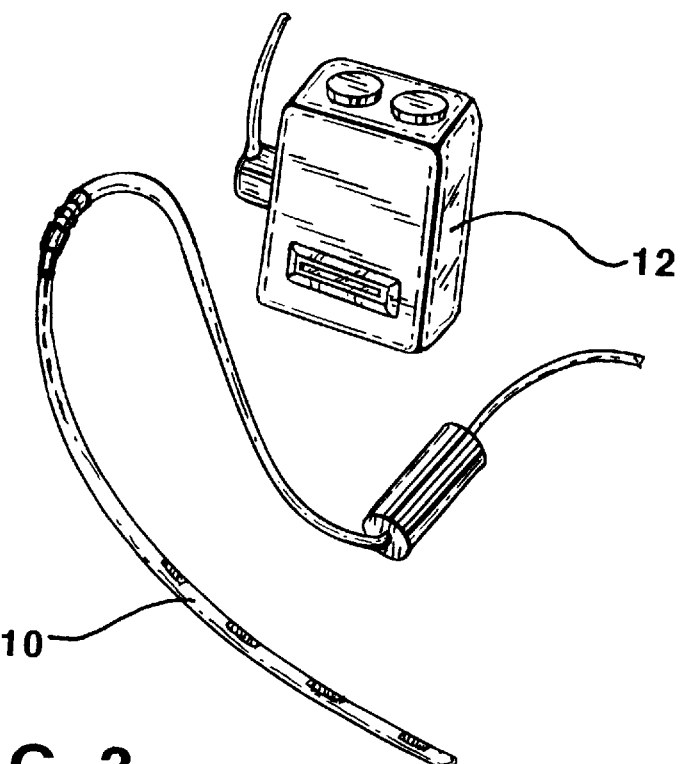
FIG. 3 is a perspective view of a screener device and a screening lead.
Figure 4:
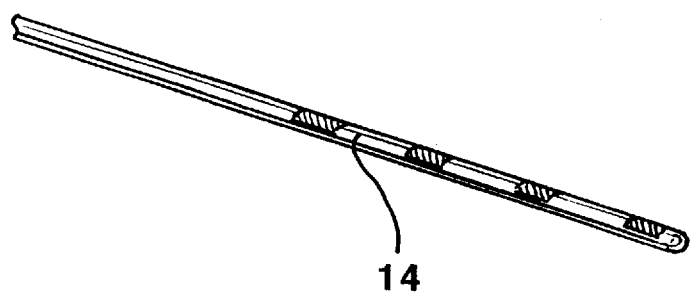
FIG. 4 is a top view of a permanent lead.
Figure 5:
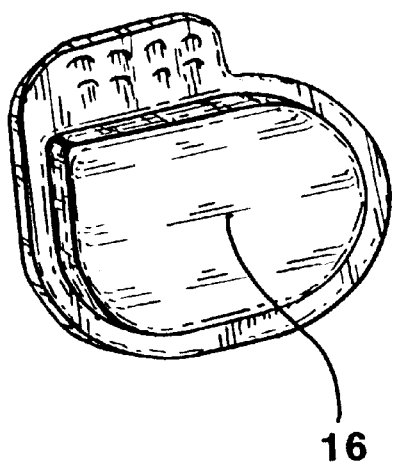
FIG. 5 is a perspective view of an implantable pulse generator (IPG).
Figure 6:
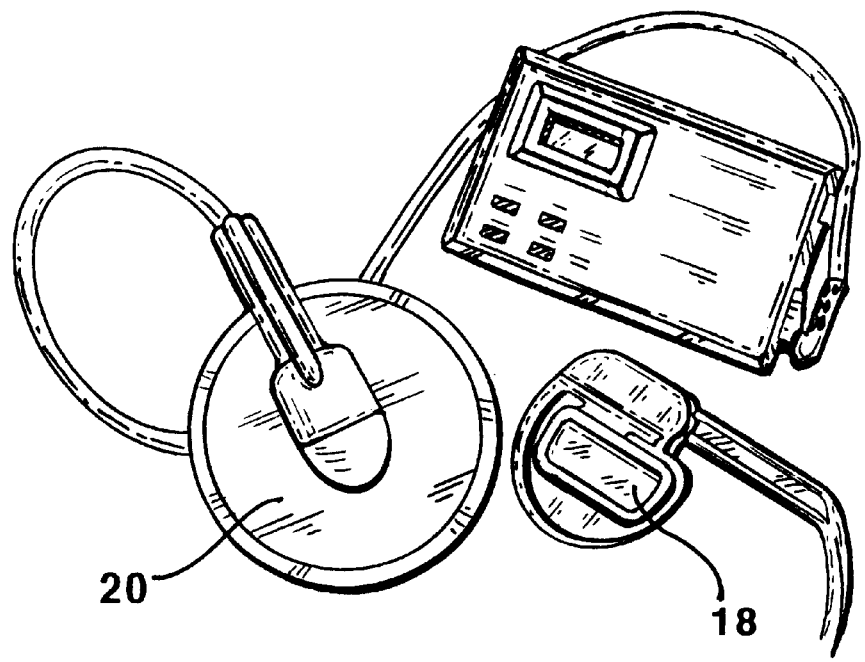
FIG. 6 is a perspective view of an RF system receiver and an RF system transmitter.

The present invention comprises a method of stimulating peripheral nerves. The method is preferentially accomplished in two stages: a test implantation and screening stage and a permanent implantation of a lead and electrical stimulation system stage. The invention contemplates using, as shown in FIG. 2, a screening lead 10 (shown in detail in FIG. 3), a screener device 12 (also shown in detail in FIG. 3), a permanent lead 14 (shown in detail in FIG. 4) and either an implanted pulse generator (IPG) 16 (shown in detail in FIG. 5) or an implanted RF system receiver 18 and its corresponding RF system transmitter 20 (shown in detail in FIG. 6).

The screening lead 10 and permanent lead 14 are preferably percutaneous leads chosen from the Pisces-Quad® family of quadripolar leads. Screener device 12 is preferably a Model 3625 Screener or a Model 3628 DualScreen® Screener. IPG 16 is preferably an Itrel® IPG. RF system receiver 18 and RF system transmitter 20 are both preferably part of an RF stimulation system such as the X-trell® or Matrix® RF Stimulation Systems. Screening lead 10, permanent lead 14, screener device 12, IPG 16, RF system receiver 18 and RF transmitter 20 are all available from Medtronic, Inc. of Minneapolis, Minn.

The method for treating pain due to peripheral nerves involves subcutaneous placement of a permanent lead 14 transversely across the peripheral nerve that is causing the pain. This peripheral nerve is subsequently electrically stimulated to cause paresthesia of the painful area. The method also preferably involves placement of a screening lead 10 and subsequent test electrical stimulation prior to placing the permanent lead 14. Although the method preferably involves placing both a screening lead 10 and then a permanent lead 14, the method also includes implanting just the permanent lead 14 as will be described in detail hereafter. For illustration purposes, the method for treating pain due to peripheral nerves will be described with reference to treating occipital neuralgia by electrically stimulating the occipital nerves.

One key to the technical success of this invention is the accurate placement of the permanent lead 14. Because of the importance of accurate placement of the permanent lead 14, accurate placement of permanent lead 14 is facilitated by the placement of the screening lead 10 and the subsequent test electrical stimulation. The steps in the invention to percutaneously place a screening lead 10 to treat occipital neuralgia will now be described in detail. These steps are given as the preferred method of implementing the invention for most patients. It is recognized, however, that the skilled physician will adapt the method described herein using his or her professional skill and judgment to the particular circumstances of a particular patient. Further, although the method of treating pain described in detail herein is specifically directed to treating occipital neuralgia, unless otherwise specifically directed, any reference to the occipital nerve or occipital neuralgia refers as well to any peripheral nerve or neuralgias corresponding to a peripheral nerve, respectively.

The first step of the test implantation and screening stage is the implantation of a screening lead 10. The method involves subcutaneous placement of a screening lead 10 in the fascia 34 above (superior to) the occipital nerve causing pain and proximal to the level of detected pain. The first step in locating the area to implant the screening lead 10 is to palpate the area of pain to identify the specific nerve that is causing the pain. If it is confirmed that an occipital nerve is causing the pain and the specific occipital nerve has been identified, an introducer needle 22 is used to place the screening lead 10.

Figure 7:
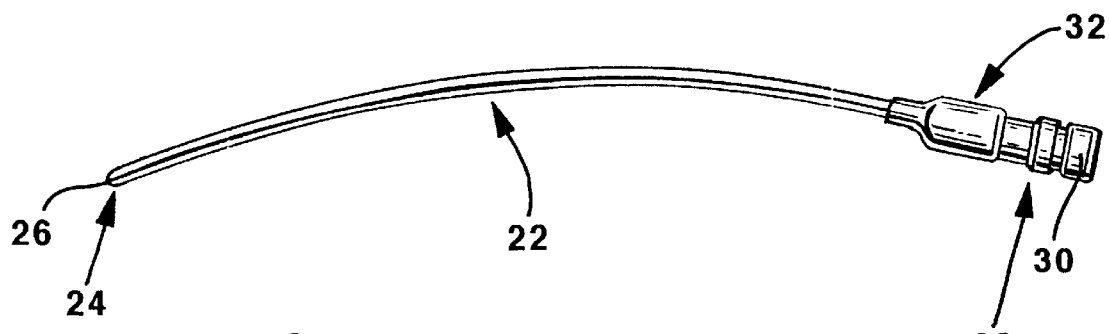
FIG. 7 is a top view of an introducer needle curved to facilitate placement of the permanent lead to treat occipital neuralgia.

The preferred embodiment for the introducer needle 22 is a Touhy needle. As shown in FIG. 7, the introducer needle 22 has a terminal end 24 that has a beveled edge 26 and a proximal end 28 that includes a hub 30. Beveled edge 26 is a sharp edge that allows the terminal end 24 to be pushed through tissue. Hub 30 allows the physician to manipulate the introducer needle 22. Hub 30 also has a notch 32 that is aligned with the beveled edge 26 to indicate the orientation of beveled edge 26 to the hub 30 by tactile sensation.

The introducer needle 22 is then subcutaneously placed in the fascia 34 above (superior to) the nerve 36 that is causing the pain. In the case of treating occipital neuralgia, the introducer needle 22 is placed in the fascia 34 above (superior to) the occipital nerve that is causing the pain. Fascia 34 is a sheet of fibrous tissue that envelops the body under the skin and also encloses the muscles. In the described method, the introducer needle 22 will be introduced into the fascia 34 so that the introducer needle will be between the patient's skin and muscle. The nerve causing the pain will be located within or under the musculature. In the case of treating occipital neuralgia, the introducer needle 22 will be introduced into the fascia 34 so that the introducer needle will be between the patient's skin and the occipital nerve.

Figure 8:
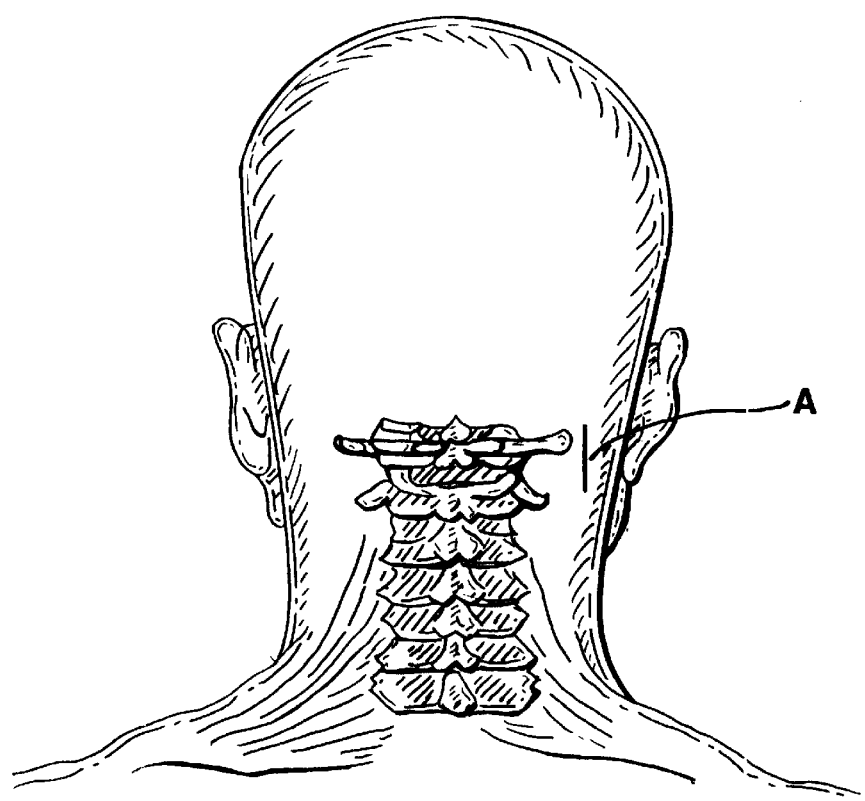
FIG. 8 is a schematic view of the entry site used to implant a screening lead or a permanent lead for treating occipital neuralgia.

The introducer needle 22 is preferably introduced through a small stab wound "A" at the needle entry site (FIG. 8). Rapid needle insertion is preferably used. This technique usually obviates the need for even a short acting general anesthetic.

Figure 9:
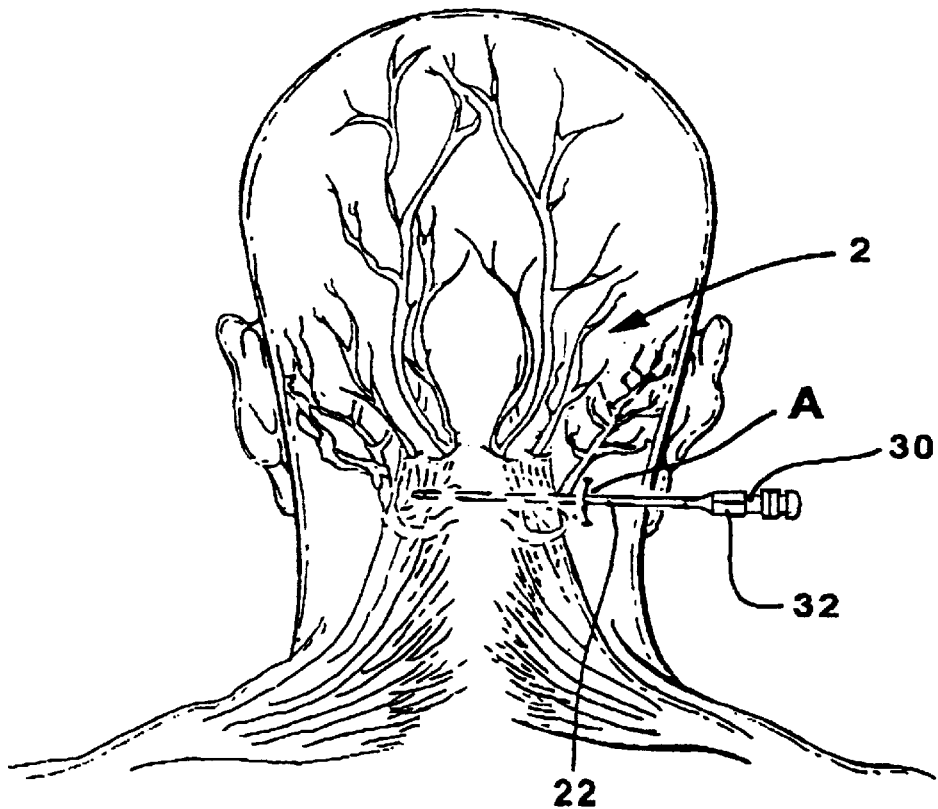
FIG. 9 is a schematic view of the placement of the introducer needle prior to placing the screening lead.
Figure 10:
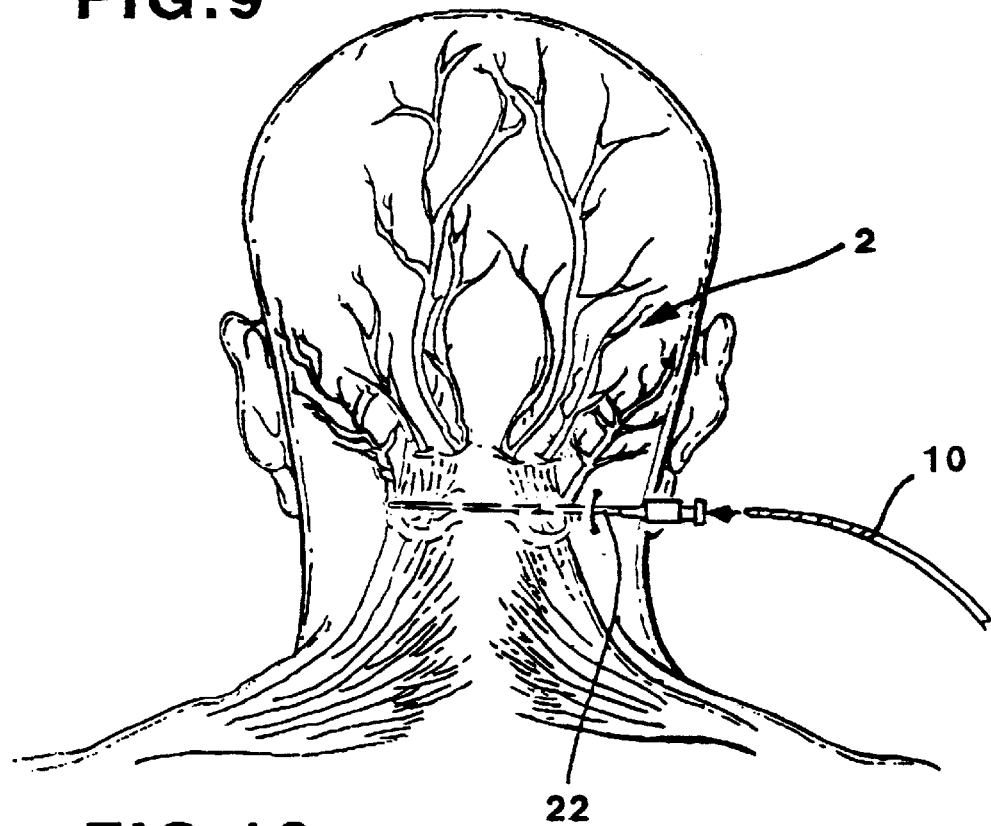
FIG. 10 is a schematic view of the placement of the introducer needle with the screening lead being inserted into the introducer needle.

The introducer needle 22 is moved through the fascia 34 to a position over the occipital nerve that is causing the pain (FIG. 9). When the introducer needle 22 is in position above the occipital nerve, the screening lead 10 is passed through the introducer needle 22 (FIG. 10) until the screening lead 10 is also in position above the occipital nerve causing the pain. Then, the introducer needle 22 is removed leaving the screening lead 10 in place above the occipital nerve.

Figure 11:
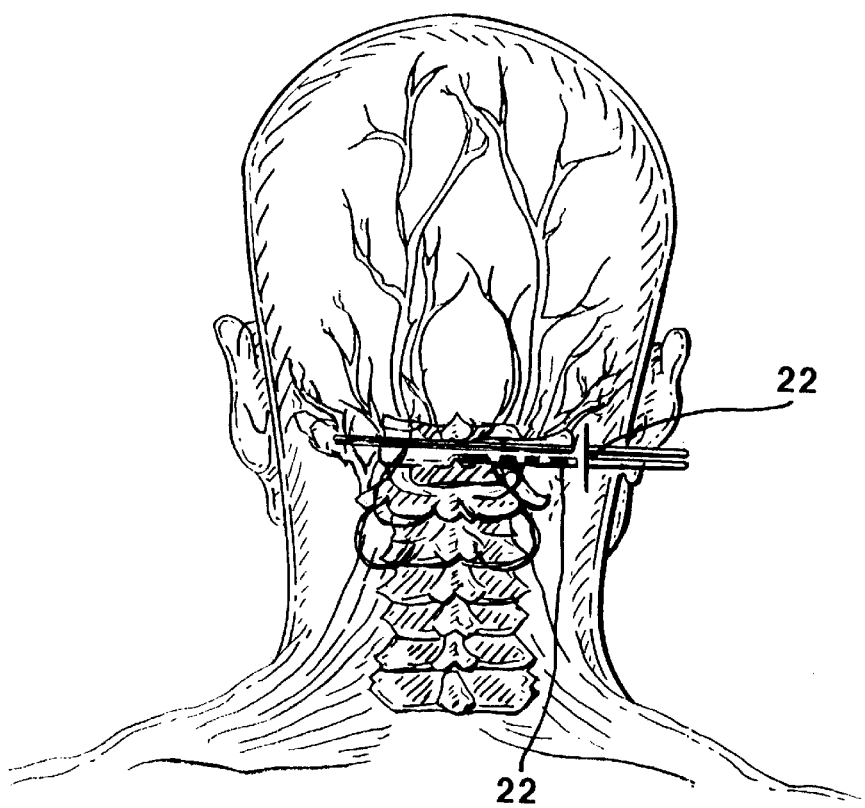
FIG. 11 is a schematic view of dual leads placed to treat bilateral pain.

Single or dual quadripolar as well as single or dual octapolar screening leads 10 may be used depending on whether the pain is unilateral (on one side of the body only) or bilateral (on both sides of the body). Where the pain is bilateral and two screening leads 10 are used (FIG. 11), each screening lead 10 will be placed as described above.

Following placement of the screening lead 10 by the introducer needle 22, the screening lead 10 is connected to the screening device 12, as is well understood in the art. With the screening lead 10 in place as described above and the screening lead 10 connected to the screening device 12, the patient is electrically stimulated by the screening lead 10 and screener device 12 to evaluate the screening lead 10 position and to develop optimal stimulation parameters. Stimulation is applied using the screener device 12 to select various electrode combinations, enabling the patient to report stimulation location, intensity and overall sensation. This allows the physician to test the stimulation and determine optimum stimulation parameters prior to permanently implanting the permanent lead 14 and the source of electrical stimulation pulses, either the IPG 16 or the RF system receiver 18. The effect of this stimulation is determined and the parameters of stimulation adjusted for optimal pain relief It is preferred that the patient be awake and alert so that the patient will provide verbal feedback regarding paresthesia coverage of the painful area to assist in determining the optimum stimulation parameter settings.

The following have been found to be typical ranges for stimulation parameters for screening by the screener device 12 and the screening lead 10 to optimize paresthesia levels for pain coverage. These parameters can vary from patient to patient and may be outside the ranges given here. Nevertheless, these representative values are given for the purpose of illustrating the invention and not for the purpose of limiting the invention. Values for these parameters may be higher or lower than the values shown.

| | |
|---|---|
| Amplitude: | 0.5–4.0 volts |
| Pulse Width: | 90–200 μsec |
| Rate: | 50–400 Hz |

If the patient reports muscle contractions (grabbing sensation) or burning, this usually indicates that the screening lead 10 is located too deep (anterior) in the subcutaneous tissue. It may also indicate that the screening lead 10 is not positioned correctly above (superior to) the nerve. It may be necessary to remove and reposition the screening lead 10. If adjustment of screening lead 10 is necessary, the screener device 12 is removed from the screening lead 10. Then, the position of the screening lead 10 is adjusted and stimulation is tested again for optimal pain relief. Adjusting the position of the screening lead 10 may mean removing the screening lead 10 and re-implanting the screening lead 10 according to the technique described above.

After good paresthesia coverage is obtained by manipulating the parameters of stimulation applied through screening lead 10, percutaneous testing wires can be externalized for the test stimulation period as is well understood in the art. This period is used to evaluate the patient's response to stimulation before complete implantation of all system components.

Alternately, once satisfactory paresthesia is confirmed, the screener device 12 may be removed from the screening lead 10 and a source of electrical stimulation pulses such as the IPG 16 or RF system receiver 18 is immediately implanted and attached to the screening lead 10. Hence, screening lead 10 in this embodiment becomes permanent lead 14. However, it is preferred that the patient use the implanted screening lead 10 and screener system 12 for several days prior to implanting a permanent stimulation system Once the screening lead 10 has been appropriately positioned and tested, if satisfactory results are obtained, the method should proceed to the "permanent implantation of a lead and electrical stimulation system" stage. The steps in the invention to permanently implant a stimulation system will now be described in detail in connection with the treatment of occipital neuralgia. As mentioned above, it is possible to implant a source of electrical stimulation pulses such as the IPG 16 or RF system receiver 18 and attached it directly to the screening lead 10 so that screening lead 10 becomes the permanent lead 14. However, the preferred embodiment of the invention contemplates removing the screening lead 10 and replacing it with a permanent lead 14.

After it has been determined that the patient is receptive to pain relief from electrically stimulating the peripheral nerve causing the pain and the paresthesia associated with the electrical stimulation has been maximized, the screener device 12 is disconnected from the stimulation lead 10 and the screening lead 10 is removed. The patient is then prepared for placement of the permanent lead 14 and the implanted pulse generator (IPG) 16 or implanted RF system receiver 18. The purpose of the "permanent implantation of a lead and electrical stimulation system" stage is to internalize (that is, implant) the permanent lead 14 and either the IPG 16 or the RF system receiver 18. Therefore, this stage includes implanting the permanent lead 14, neurostimulator (either IPG 16 or RF system receiver 18) and any extension sometimes used to connect permanent lead 14 and either IPG 16 or RF system receiver 18 as is well understood in the art.

As stated above, one key to the technical success of this invention is the accurate placement of the permanent lead 14. It is therefore crucial to the success of the invention to have a lead placement for the permanent lead 14 that results in paresthesia that covers the patient's painful area. Therefore, lead placement is preferably determined using patient feedback during intraoperative testing of the efficacy of the permanent lead 14 placement and the stimulation parameters. Performing implantation of the permanent lead 14 under local anesthetic allows for this feedback.

Figure 12:
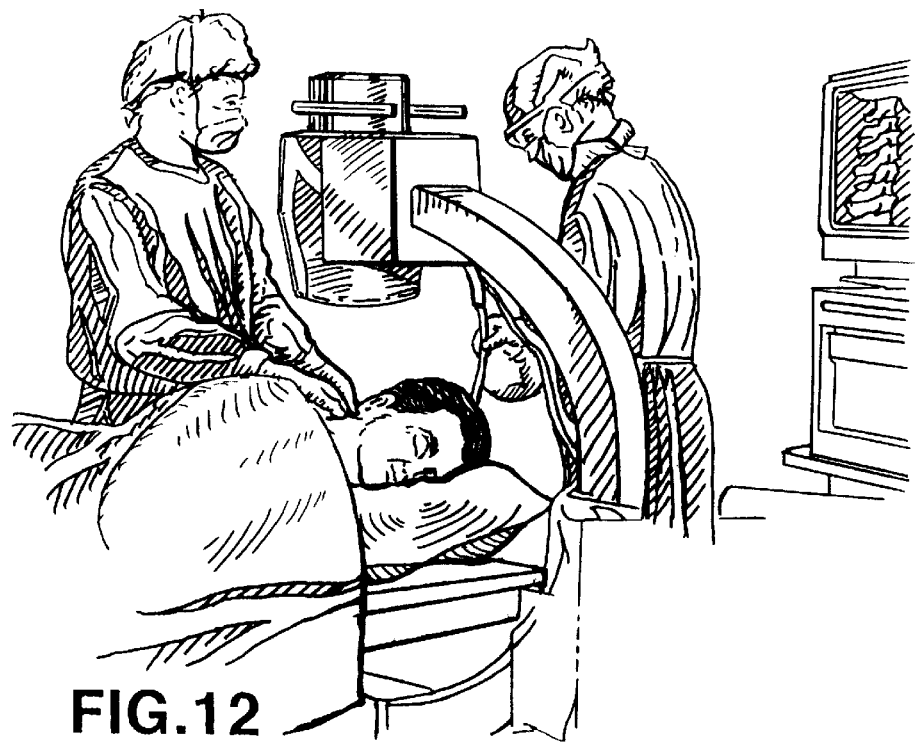
FIG. 12 is a perspective view of a patient prior to being implanted with a permanent lead.

A local anesthetic is preferably used in the area of the introducer needle 22 entry site to ensure the patient is alert and able to respond during the procedure. To help the patient relax, sedatives are also preferably administered intravenously. Prophylactic antibiotics can also be administered intravenously for protection from postoperative infection. As a result, the patient is preferably awake and alert during the placement of the permanent lead 14 and the subsequent test stimulation.

Where treating occipital neuralgia, the patient is preferably placed in a lateral position, or in a prone position with the head to the side, on a radiolucent table (FIG. 12). The patient is prepared and draped according to standard surgical procedure. Fluoroscopy is used to identify the location of the C1 vertebra. The location and midline of the C1 vertebra is marked on the patient's skin with a sterile marker.

A Touhy needle is preferably used as an introducer needle 22 to introduce permanent lead 14. The introducer needle 22 includes a stylet 42. The introducer needle 22 is manually gently curved by the physician to conform to the contour of the patient's body above the peripheral nerve to facilitate placement of the permanent lead 14. Where the peripheral nerve is the occipital nerve, the introducer needle 22 is manually gently curved by the physician to conform to the contour of the patient's neck (FIG. 7) to facilitate placement of the permanent lead 14.

A small stab wound "A" is made at the needle entry site (FIG. 8) at the C1 level. Using local anesthesia, a 2 cm. vertical skin incision is made in the patient's neck lateral to the midline of the spine at the level of C1. The introducer needle 22 is introduced into the subcutaneous tissue, superficial to the fascia 34 and muscle layer but below the skin, without further dissection across the trunk of the occipital nerves. These nerves are located within the cervical musculature and overlying fascia 34.

Figure 13:
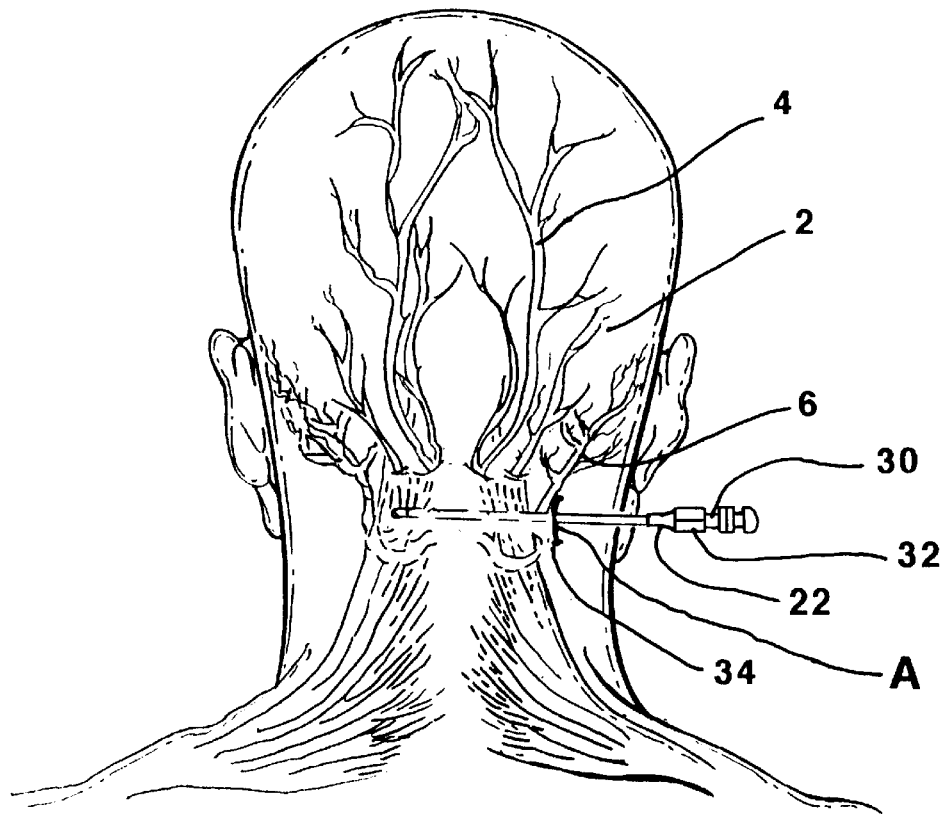
FIG. 13 is a schematic view of the placement of the introducer needle prior to placing the permanent lead.

The physician then advances the introducer needle 22 transversely from the lateral incision point to and across the midline of the spine under fluoroscopic observation to the appropriate location above the trunk of the occipital nerve FIG. 13). The beveled edge 26 of the introducer needle 22 should face toward the front of the body (anterior). The orientation of the beveled edge 26 can be verified by referring to the notch 32 on the needle hub 30 of the introducer needle 22.

The curve of the introducer needle 22 may be checked, if desired, by the physician by removing and re-inserting the needle stylet 42. A useful, curved introducer needle 22 is ensured if it is easy to remove and reinsert the stylet 42 within the introducer needle 22. If desired, an additional check can be made by removing the stylet 42, then carefully inserting the permanent lead 14 through the introducer needle 22 to just beyond the beveled edge 26 of the introducer needle 22. If the curvature of the introducer needle 22 is correct, the permanent lead 14 should pass easily to just beyond the beveled edge 26 of the introducer needle 22. The permanent lead 14 is then removed and the stylet 42 re-inserted into the introducer needle 22.

Figure 14:
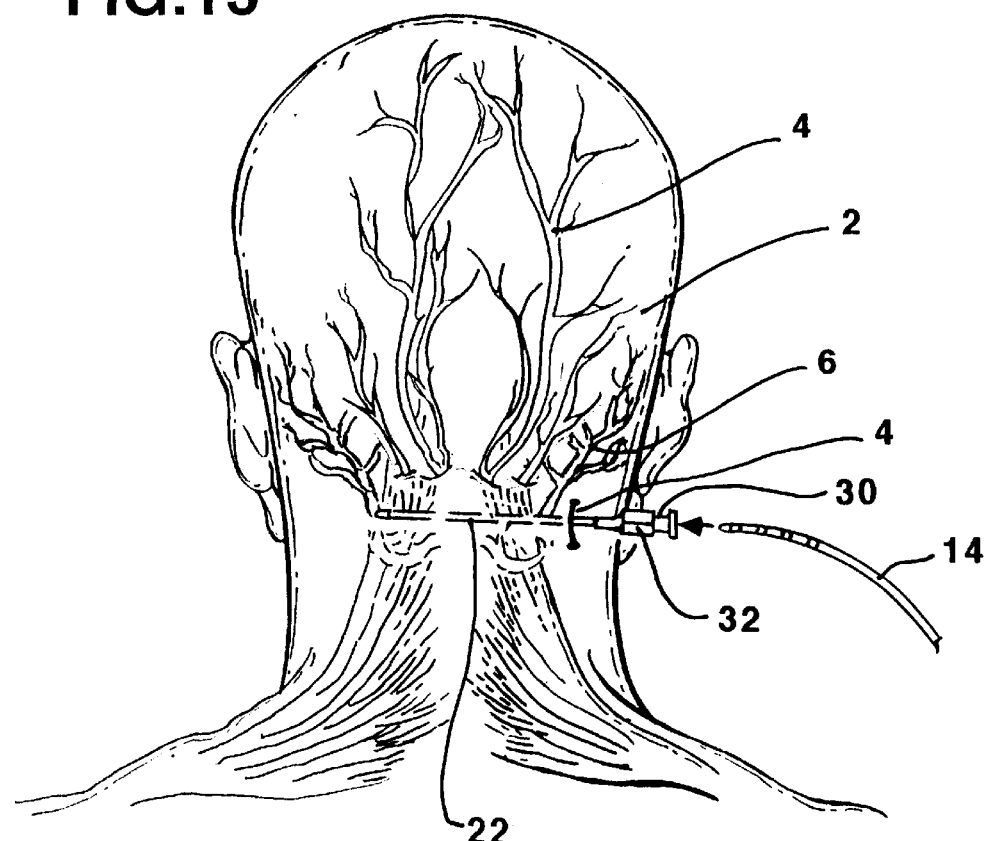
FIG. 14 is a schematic view of the placement of the introducer needle with the permanent lead being inserted into the introducer needle.

Once the desired position has been reached, the stylet 42 is removed from the introducer needle 22. The permanent lead 14 is slowly inserted through the introducer needle 22 until the distal tip 36 of the permanent lead 14 just exits the introducer needle 22 (FIG. 14). Then, the introducer needle 22 is carefully removed over the permanent lead 14. The permanent lead 14's placement is verified with fluoroscopy. Alternately, the introducer needle 22 can be partially removed. This allows the electrode contacts on the permanent lead 14 to be exposed while facilitating introducer needle 22 reinsertion if repositioning of the permanent lead 14 is needed. Fluoroscopy is used to ensure that all electrodes of the permanent lead 14 are exposed. If necessary, the introducer needle 22 may be adjusted to move the permanent lead 14 to a location where the permanent lead 14 will optimally stimulate the targeted occipital nerve(s).

If more than one permanent lead 14 is to be implanted, for example, on each side of the midline to treat bilateral pain, the procedure described above is repeated for each such permanent lead 14.

Following placement of the permanent lead 14 by the introducer needle 22, the permanent lead 14 is again connected to the screening device 12, as is well understood in the art. This allows the physician to test the stimulation and confirm that paresthesia is obtained with the placement of the permanent lead 14 prior to permanently implanting the IPG 16 or the RF system receiver 18. Since the patient is preferably awake and alert, the patient will provide verbal feedback regarding paresthesia coverage of the painful area to assess the placement of the permanent lead 14.

If the patient reports muscle contractions (grabbing sensation) or burning, this usually indicates that the electrodes on the permanent lead 14 are too deep (anterior) in the subcutaneous tissue. It may also indicate that the electrodes are significantly above or below the C1 landmark. It may be necessary to remove and reposition the permanent lead 14. If adjustment of permanent lead 14 is necessary, the screener device 12 is removed from the permanent lead 14. Then, the position of the permanent lead 14 is adjusted and stimulation is tested again.

Figure 15:
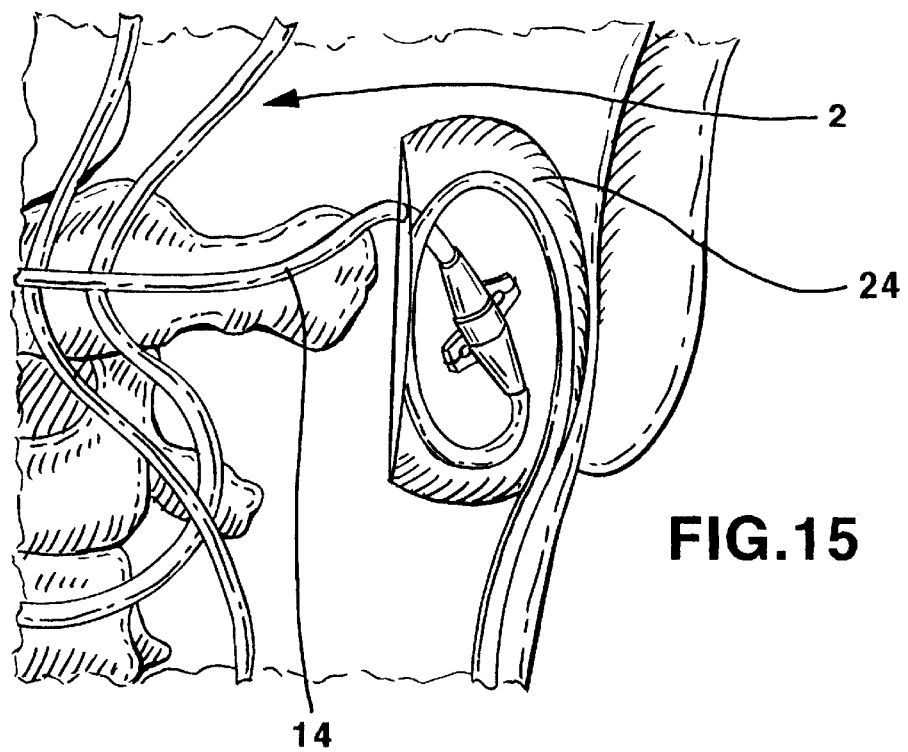
FIG. 15 is a schematic view of the location of the subcutaneous pocket for housing the loop of the permanent lead and the lead anchor.

After good paresthesia coverage is obtained, the screener device 12 is removed from the permanent lead 14. It is now possible to implant the source of electrical stimulation pulses such as the IPG 16 or RF system receiver 18 and any extension sometimes used to connect permanent lead 14 and either IPG 16 or RF system receiver 18 as is well understood in the art. Internalization of the neurostimulation system for occipital nerve stimulation preferably follows the protocol used for other Peripheral Nerve Stimulation (PNS) indications as is well understood in the art. Basically, the procedure involves creating a subcutaneous pocket 24 in tissue (FIG. 15), anchoring the permanent lead 14, implanting the IPG 16 or RF system 18, tunneling the permanent lead 14 and connecting the permanent lead 14 to the IPG 16 or RF system 18 as is well understood in the art.

The following have been found to be typical ranges for stimulation parameters applied to the permanent lead 14 to obtain optimum paresthesia levels for pain coverage to treat occipital neuralgia. These values can vary from patient to patient and may be outside the ranges given here. Nevertheless, these representative values are given for the purpose of illustrating the invention and not for the purpose of limiting the invention. Again, values for these parameters may be higher or lower than the values shown.

| | |
|---|---|
| Amplitude: | 0.5–4.0 volts |
| Pulse Width: | 90–200 μsec |
| Rate: | 50–400 Hz |

These steps are given as the preferred method of implementing the invention for most patients. It is recognized, however, that the skilled physician will adapt the method described herein using his or her professional skill and judgment to the particular circumstances of a particular patient.

A specific example of percutaneous nerve stimulation has been given for treating occipital neuralgia. Although the method of treating occipital neuralgia has been described in detail, the steps described can be adapted to treating other peripheral nerve applications as medical judgment and necessity require. Examples of other applications for the described subcutaneous PNS technique include peripheral nerves in the head and neck, trunk and limbs. Examples of neuralgias in the head and neck that can be treated by stimulating peripheral nerves include, but are not limited to, post herpetic neuralgia, chronic deafferentation pain, chronic peripheral nerve pain, post craniotomy pain and incisional pain. For post herpetic neuralgia, the permanent lead 14 should preferably be placed in the vicinity of the supraorbital nerve in the forehead area. For chronic deafferentation pain, the permanent lead 14 should preferably be placed subcutaneously in the vicinity of the deafferentation pain. For chronic peripheral nerve pain, the permanent lead 14 should preferably be placed proximal to any peripheral nerve throughout the body. For chronic post craniotomy pain, the permanent lead 14 should preferably be placed in the region of the craniotomy incision.

Examples of neuralgias in the trunk that can be treated by stimulating peripheral nerves include, but are not limited to, clunial nerve pain, post herniorrhapy pain, localized low back or other spine pain and incisional neuroma pain. For clunial nerve pain, the permanent lead 14 should preferably be placed over the clunial nerve in the buttock area. For post herniorrhapy pain, the permanent lead 14 should preferably be placed subcutaneously in the region of the iliolinguinal nerve. For localized low back or other spine pain, the permanent lead 14 should preferably be placed in the vicinity of the localized area of pain. For incisional neuroma pain, the permanent lead 14 should preferably be subcutaneously placed in the region of the incisional neuroma.

Figure 16:
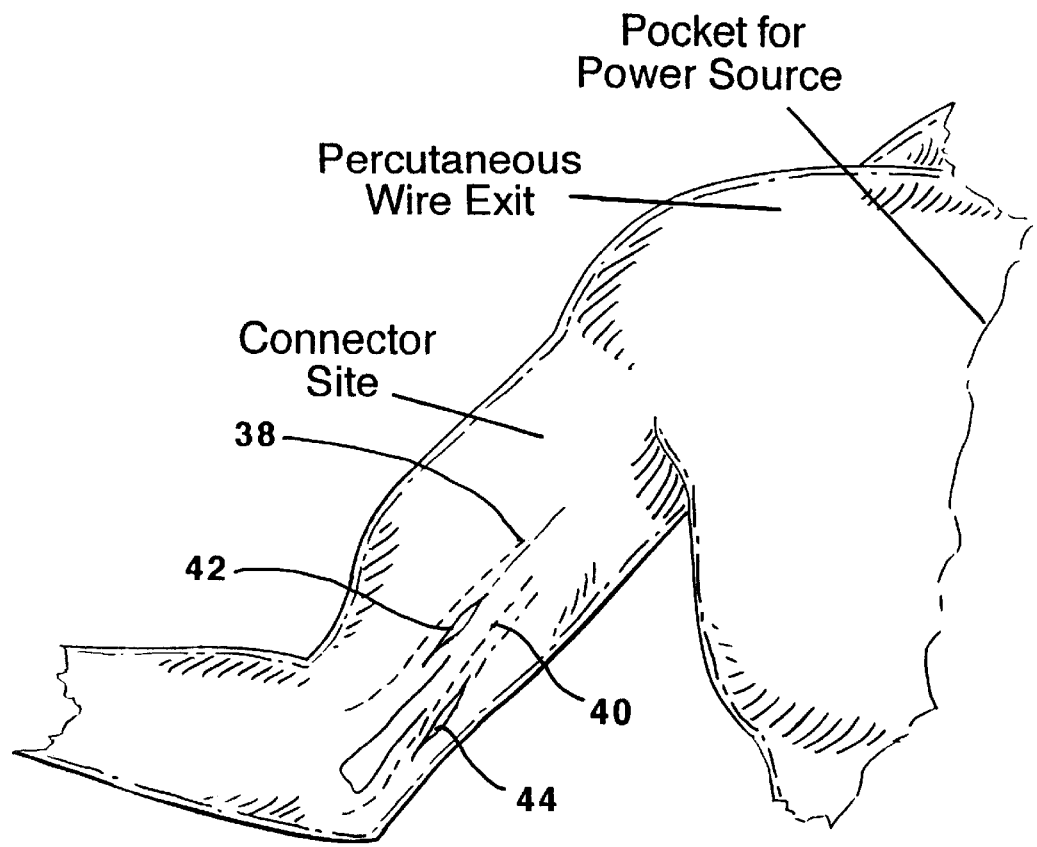
FIG. 16 is a perspective view of a human torso and arm showing the location of the leads for two embodiments of the invention.
Figure 17:
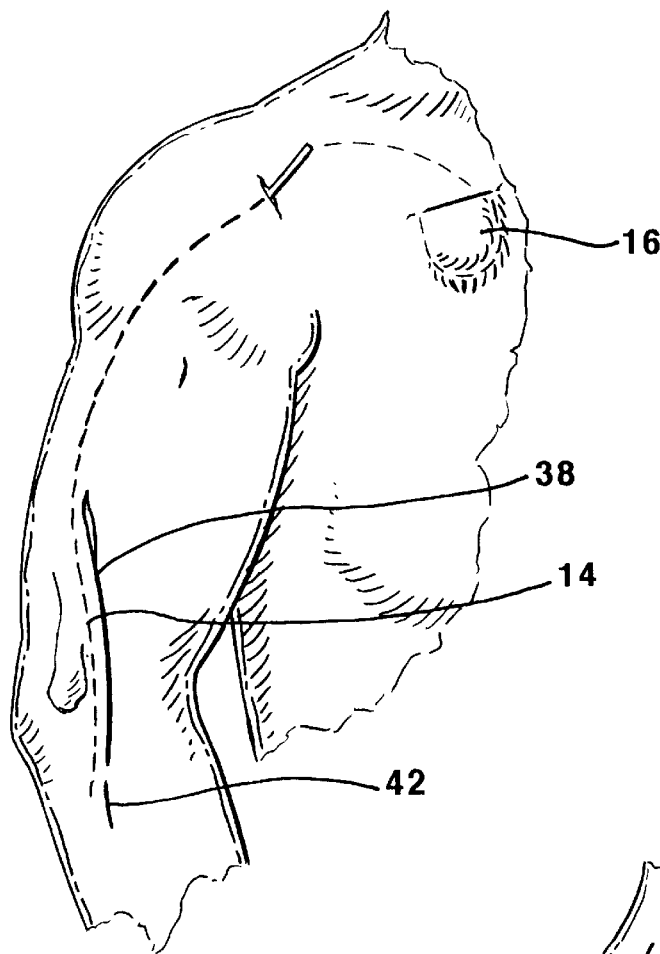
FIG. 17 is a perspective view of a human torso and arm showing the exit sites of the leads and preferred location for an IPG for the method of FIG. 16.

Examples of neuralgias in the limbs that can be treated by stimulating peripheral nerves include, but are not limited to, stump neuroma pain, incisional scar pain, deafferention pain and chronic peripheral nerve pain as for example with the median nerve or ulnar nerve. For stump neuroma pain, the permanent lead 14 should preferably be subcutaneously placed in the region of the neuroma. For incisional scar pain, the permanent lead 14 should preferably be subcutaneously placed in the region of the incision. For chronic peripheral nerve pain of the medial nerve or ulnar nerve, the permanent lead 14 should preferably be placed over the medial nerve 38 or ulnar nerve 40, respectively, as shown in FIG. 16. Here, the technique described above is applied to the placement of screening lead 10 and permanent lead 14 with the leads 10, 14 located above (superior to) the desired peripheral nerve through medial nerve incision site 42 and ulnar nerve incision site 44, respectively. Once the permanent lead 14 is in place, the IPG 16 or RF system receiver 18 is implanted as is well understood in the art (FIG. 17) and connected to the permanent lead 14.

Figure 18:
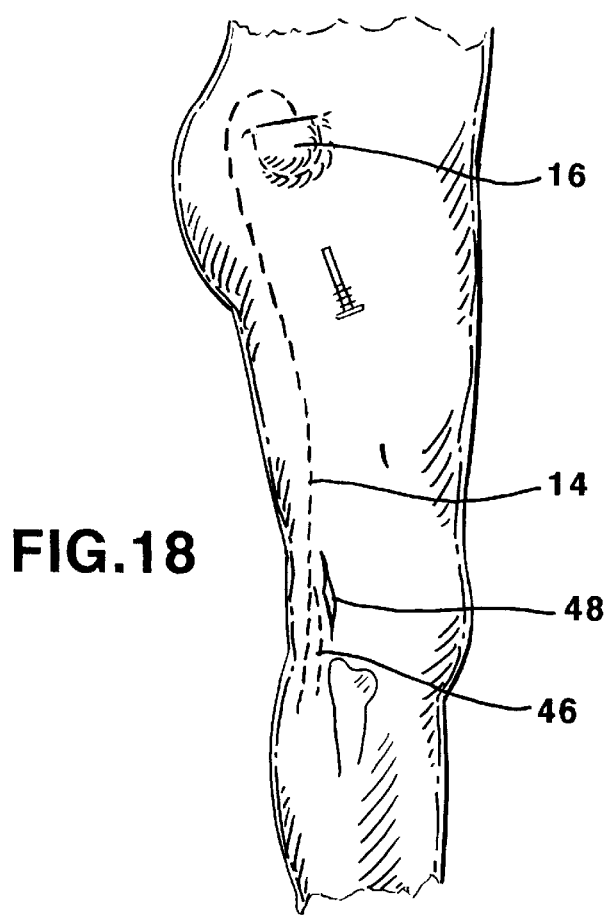
FIG. 18 is a perspective view of a human leg showing the location of a lead and IPG for an embodiment of the invention.

FIGS. 18 shows the placement of a permanent lead 14 next to the sciatic nerve 46 in the leg. Permanent lead 14 is implanted as described above through the sciatic nerve incision site 48. Placement of permanent lead 14 and the subsequent electrical stimulation of the sciatic nerve 46 could treat neuromas or chronic pain emanating from this peripheral nerve.

Figure 19:
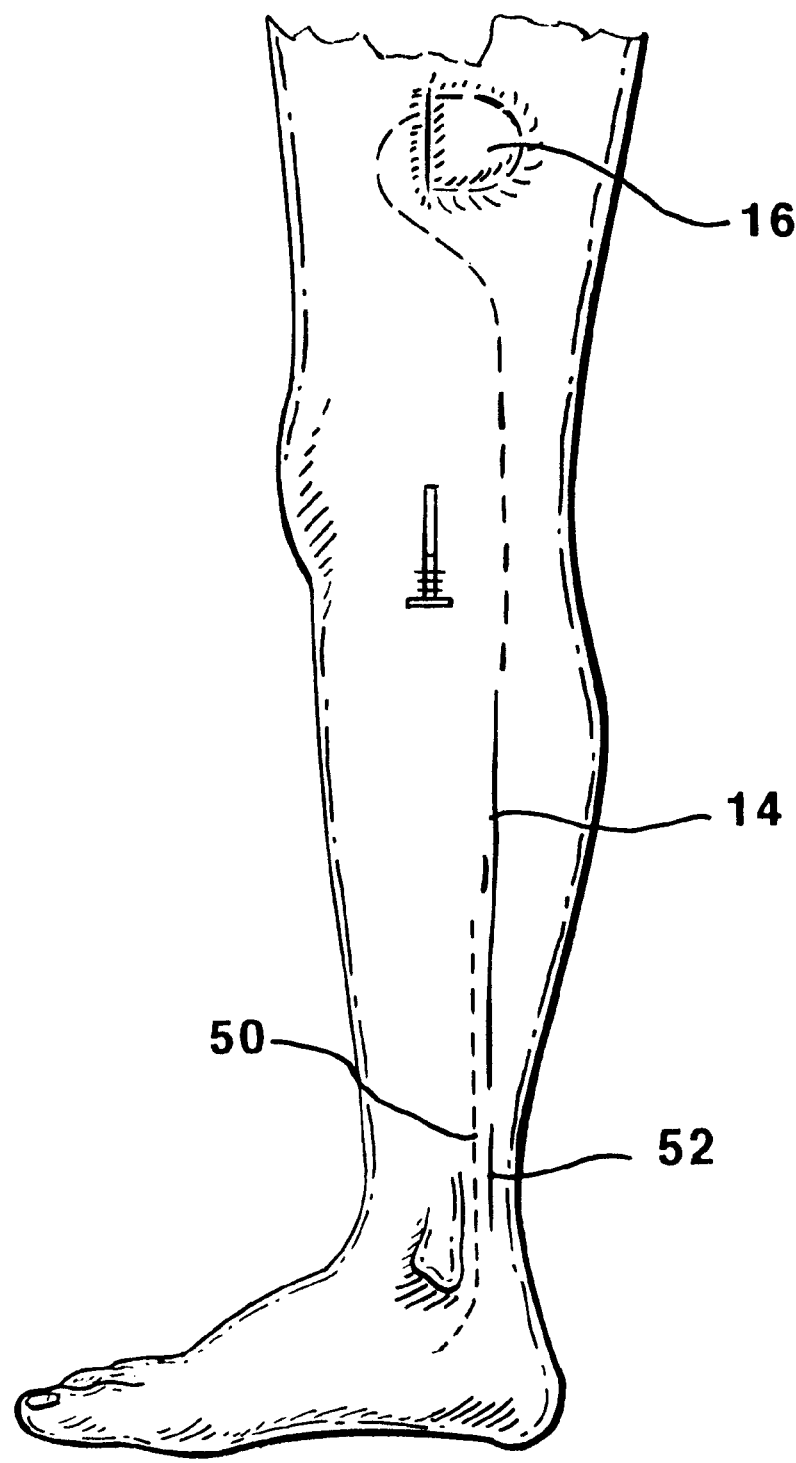
FIG. 19 is a perspective view of a human leg showing the location of a lead and IPG for another embodiment of the invention.

Further, FIG. 19 shows the placement of a permanent lead 14 next to a peripheral nerve 48 in the ankle, foot or other localized are of pain. Permanent lead 14 is implanted as described above through a peripheral nerve incision site 50. Placement of permanent lead 14 and the subsequent electrical stimulation of the affected peripheral nerve 44 could also treat neuromas in or around this peripheral nerve and also chronic pain arising from this nerve.

The examples of the method of the invention shown in FIGS. 16–19 have been given to illustrate examples of peripheral nerves to which the present method could apply. The application of the present invention to other peripheral nerves with their corresponding maladies and neuromas will occur to those skilled in the art. Conversely, once neurological maladies or neuromas and their corresponding peripheral nerves have been identified, as will also occur to those skilled in the art, the present invention may be used to treat such maladies or neuromas. It is clear that those skilled in the art will be able to practice the invention described above as applied to any peripheral nerve or to treat any particular neuroma by applying the disclosed method to its corresponding peripheral nerve.

The description contained herein is intended to be illustrative and not exhaustive. Many variations and alternatives will occur to one of ordinary skill in this art. All these alternatives and variations are intended to be included within the scope of the attached claims. Those familiar with the art may recognize other equivalents to the specific embodiments described herein which equivalents are also intended to be encompassed by the claims attached hereto.

I claim:

1. A method of stimulating a peripheral nerve to treat pain emanating from the peripheral nerve, the method comprising the steps of:
    placing a lead having at least one electrode in fascia superior to and near the peripheral nerve that is causing pain so that at least one electrode is in the fascia; and
    electrically stimulating the peripheral nerve with the at least one electrode in the fascia to cause paresthesia of the painful area.

2. The method of claim 1 wherein the step of placing a lead includes the step of placing a lead across the peripheral nerve that is causing pain.

3. The method of claim 2 wherein the step of placing a lead across the peripheral nerve that is causing pain includes the step of subcutaneously placing a lead across the peripheral nerve that is causing pain.

4. The method of claim 1 wherein the step of placing a lead in the fascia superior to the peripheral nerve includes the step of placing a lead in the fascia superior to the peripheral nerve proximal to a level of detected pain.

5. The method of claim 1 wherein the step of placing a lead includes the step of subcutaneously placing a lead near the peripheral nerve that is causing pain.

6. The method of claim 1 further comprising the step of initially palpating the area of pain to identify the specific peripheral nerve that is causing the pain.

7. The method of claim 1 wherein the step of placing a lead includes the steps of:
    providing an introducer needle;
    subcutaneously placing the introducer needle in the fascia superior to the peripheral nerve that is causing pain.

8. The method of claim 7 wherein the step of placing a lead further includes the step of passing, when the introducer needle is in position above the peripheral nerve, the lead through the introducer needle until the lead is also in position above the peripheral nerve causing the pain.

9. The method of claim 8 further comprising the step of removing, after passing the lead through the introducer needle until the lead is also in position above the peripheral nerve causing the pain, the introducer needle leaving the lead in place above the peripheral nerve.

10. The method of claim 7 wherein the step of subcutaneously placing the introducer needle in the fascia superior to the peripheral nerve that is causing pain includes the step of curving the introducer needle to conform to the contour of the patient's body superior to the peripheral nerve.

11. The method of claim 1 wherein the step of placing a lead includes the step of placing dual leads.

12. The method of claim 11 further comprising the step of connecting the lead to a screening device.

13. The method of claim 12 further comprising the step of performing test electrical stimulation with the lead.

14. The method of claim 13 wherein the steps of performing test electrical stimulation with the lead includes the step of electrically stimulating the patient by the lead and screener device and evaluating the lead position from the patient's response to the step of electrically stimulating the patient.

15. The method of claim 13 wherein the step of performing test electrical stimulation with the lead includes the step of electrically stimulating the patient by the lead and screener device and developing optimal stimulation parameters based on the patient's response to the step of electrically stimulating the patient.

16. The method of claim 13 further comprising the step of receiving verbal feedback from the patient regarding paresthesia coverage of the effects of the electrical stimulation by the lead.

17. The method of claim 13 wherein the step of performing test electrical stimulation with the lead includes the step of electrically stimulating the patient with an electrical signal having an amplitude between about 0.5 to about 4.0 volts.

18. The method of claim 13 wherein the step of performing test electrical stimulation with the lead includes the step of electrically stimulating the patient with an electrical signal having a rate between about 50 Hz. to about 400 Hz.

19. The method of claim 13 wherein the step of electrically stimulating the patient with an electrical signal having a rate between about 50 Hz. to about 400 Hz. includes the step of electrically stimulating the patient with an electrical signal having a pulse width between about 90 sec to about 200 μsec.

20. The method of claim 1 further comprising the steps of:
implanting an implantable pulse generator; and
electrically connecting the implantable pulse generator to the lead.

21. The method of claim 1 further comprising the steps of implanting a RF system receiver; and
electrically connecting the RF system receiver to the lead.

22. The method of claim 1 wherein the step of placing a lead near a peripheral nerve that is causing pain includes the step of placing a screening lead near a peripheral nerve that is causing pain; and
wherein the step of electrically stimulating the peripheral nerve with the lead to cause paresthesia of the painful area includes the step of electrically stimulating the peripheral nerve with the screening lead; and
further comprising the steps of
placing a permanent lead near the peripheral nerve that is causing pain; and
electrically stimulating the peripheral nerve with the permanent lead to cause paresthesia of the painful area.

23. The method of claim 22 wherein the step of placing a permanent lead includes the step of placing a permanent lead across the peripheral nerve that is causing pain.

24. The method of claim 23 wherein the step of placing a permanent lead across the peripheral nerve that is causing pain includes the step of subcutaneously placing a permanent lead across the peripheral nerve that is causing pain.

25. The method of claim 22 wherein the step of placing a permanent lead includes the step of subcutaneously placing a permanent lead near the peripheral nerve that is causing pain.

26. A method of stimulating an occipital nerve to treat occipital neuralgia comprising the steps of:
placing a lead having at least one electrode in fascia superior to and near the occipital nerve that is causing pain so that at least one electrode is in the fascia;
electrically stimulating the occipital nerve with the at least one electrode in the fascia to cause paresthesia of the painful area.

27. The method of claim 26 wherein the step of placing a lead includes the step of placing a lead across the occipital nerve that is causing pain.

28. The method of claim 27 wherein the step of placing a lead across the occipital nerve that is causing pain includes the step of subcutaneously placing a lead across the occipital nerve that is causing pain.

29. The method of claim 26 wherein the step of placing a lead includes the step of subcutaneously placing a lead near the occipital nerve that is causing pain.

30. The method of claim 26 wherein the step of placing a lead near an occipital nerve that is causing pain includes the step of subcutaneously placing a lead at the level of C1 transversely across the base of the occipital nerve trunk and wherein the step of electrically stimulating the occipital nerve with the lead to cause paresthesia of the painful area includes the step of electrically stimulating the occipital nerve trunk.

31. A method of stimulating a peripheral nerve to treat pain emanating from the peripheral nerve, the peripheral nerve chosen from a group consisting of a supraorbital nerve, a clunial nerve, an iliolinguinal nerve, a median nerve, an ulnar nerve and a sciatic nerve, the method comprising the steps of:
placing a lead having at least one electrode in fascia superior to and near the peripheral nerve that is causing pain so that at least one electrode is in the fascia; and
electrically stimulating the peripheral nerve with the at least one electrode in the fascia to cause paresthesia of the painful area.

32. The method of claim 31 wherein the step of placing a lead includes the step of placing a lead across the peripheral nerve that is causing pain.

33. The method of claim 32 wherein the step of step of placing a lead across the peripheral nerve that is causing pain includes the step of subcutaneously placing a lead across the peripheral nerve that is causing pain.

34. The method of claim 31 wherein the step of placing a lead includes the step of subcutaneously placing a lead near the peripheral nerve that is causing pain.

35. The method of claim 31 wherein the step of placing a lead near a peripheral nerve that is causing pain includes the step of placing a screening lead near a peripheral nerve that is causing pain; and
wherein the step of electrically stimulating the peripheral nerve with the lead to cause paresthesia of the painful area includes the step of electrically stimulating the peripheral nerve with the screening lead to cause paresthesia of the painful area.

36. The method of claim 35 further comprising the steps of
placing a permanent lead near the peripheral nerve that is causing pain; and
electrically stimulating the peripheral nerve with the permanent lead to cause paresthesia of the painful area.

37. A method of stimulating a peripheral nerve to treat neuralgias emanating from the peripheral nerve, the method comprising the steps of:
placing a lead having at least one electrode in fascia superior to and near the peripheral nerve that is causing the neuralgia emanating from the peripheral nerve so that at least one electrode is in the fascia; and
electrically stimulating the peripheral nerve with the at least one electrode in the fascia to cause paresthesia of the area producing the neuralgia.

38. The method of claim 37 wherein the step of placing a lead includes the step of placing a lead across the peripheral nerve that is causing pain.

39. The method of claim 38 wherein the step of step of placing a lead across the peripheral nerve that is causing pain includes the step of subcutaneously placing a lead across the peripheral nerve that is causing pain.

40. The method of claim 37 wherein the step of placing a lead includes the step of subcutaneously placing a lead near the peripheral nerve that is causing pain.

41. The method of claim 37 wherein the step of placing a lead near a peripheral nerve that is causing pain includes the step of placing a screening lead near a peripheral nerve that is causing pain; and wherein the step of electrically stimulating the peripheral nerve with the lead to cause paresthesia of the painful area includes the step of electrically stimulating the peripheral nerve with the screening lead to cause paresthesia of the painful area.

42. The method of claim 41 further comprising the steps of:

placing a permanent lead near the peripheral nerve that is causing pain; and electrically stimulating the peripheral nerve with the permanent lead to cause paresthesia of the painful area.

43. A method of stimulating a peripheral nerve to treat neuralgias emanating from the peripheral nerve, the neuralgias chosen from a group consisting of post herpetic neuralgia, chronic deafferentation pain, chronic peripheral nerve pain, post craniotomy pain, incisional pain, clunial nerve pain, post herniorrhapy pain, localized low back or other spine pain, incisional neuroma pain, stump neuroma pain, incisional scar pain, deafferention pain, chronic peripheral nerve pain, sciatic neuralgia, medial neuralgia and ulnar neuralgia, the method comprising the steps of:

placing a lead having at least one electrode in fascia superior to and near the peripheral nerve that is causing the neuralgia emanating from the peripheral nerve so that at least one electrode is in the fascia; and electrically stimulating the peripheral nerve with the at least one electrode in the fascia to cause paresthesia of the area producing the neuralgia.

44. The method of claim 43 wherein the step of placing a lead includes the step of placing a lead across the peripheral nerve that is causing pain.

45. The method of claim 44 wherein the step of step of placing a lead across the peripheral nerve that is causing pain includes the step of subcutaneously placing a lead across the peripheral nerve that is causing pain.

46. The method of claim 43 wherein the step of placing a lead includes the step of subcutaneously placing a lead near the peripheral nerve that is causing pain.

47. The method of claim 43 wherein the step of placing a lead near a peripheral nerve that is causing pain includes the step of placing a screening lead near a peripheral nerve that is causing pain; and wherein the step of electrically stimulating the peripheral nerve with the lead to cause paresthesia of the painful area includes the step of electrically stimulating the peripheral nerve with the screening lead to cause paresthesia of the painful area.

48. The method of claim 47 further comprising the steps of:

placing a permanent lead near the peripheral nerve that is causing pain; and electrically stimulating the peripheral nerve with the permanent lead to cause paresthesia of the painful area.

* * * * *

UNITED STATES PATENT AND TRADEMARK OFFICE
CERTIFICATE OF CORRECTION

PATENT NO. : 6,505,075 B1
DATED : January 7, 2003
INVENTOR(S) : Richard L. Weiner It is certified that error appears in the above-identified patent and that said Letters Patent is hereby corrected as shown below:

Column 11,
Line 28, please delete "90 sec" and insert therefor -- 90 µsec. --

Signed and Sealed this

Twenty-third Day of November, 2004

JON W. DUDAS
*Director of the United States Patent and Trademark Office*

(12) EX PARTE REEXAMINATION CERTIFICATE (7641st)
United States Patent
Weiner

(10) Number: US 6,505,075 C1
(45) Certificate Issued: Jul. 27, 2010

(54) PERIPHERAL NERVE STIMULATION METHOD

(76) Inventor: Richard L. Weiner, 5950 Lindenshire La., #408, Dallas, TX (US) 75230

Reexamination Request:
No. 90/010,415, Mar. 6, 2009

Reexamination Certificate for:
Patent No.: 6,505,075
Issued: Jan. 7, 2003
Appl. No.: 09/577,258
Filed: May 22, 2000

Related U.S. Application Data

(60) Provisional application No. 60/136,690, filed on May 29, 1999.

(51) Int. Cl.
*A61N 1/18* (2006.01)

(52) U.S. Cl. ........................................ 607/46
(58) Field of Classification Search ........................ None
See application file for complete search history.

(56) References Cited

U.S. PATENT DOCUMENTS 4,512,351 A  4/1985 Pohndorf

FOREIGN PATENT DOCUMENTS

WO  WO 97/49453  12/1997

OTHER PUBLICATIONS

Illustrated Notes in Regional Anesthesia by Andrew M. Elizaga, M.D., May 1997 article on Brachial Plexus Anatomy at http://depts.washington.edu/anesth/regional/brachialplexusanatomy.html viewed on May 7, 2010.*

Erickson, Donald L., "Percutaneous trial of stimulation for patient selection for implantable stimulating devices," Oct. 1975, pp. 440–444, vol. 43, Journal of Neurosurgery.

Oh, Michel Y., et al., "Peripheral Nerve Stimulation for the Treatment of Occipital Neuralgia and Transformed Migraine Using a C1–2–3 Subcutaneous Paddle Style Electrode: A Technical Report," 2004, pp. 103–112, vol. 7, No. 2, International Neuromodulation Society.

Sheridan Butler, David. Mobilisation of the Nervous System, 1991, pp. Cover page, copyright page, table of contents page, and pp. 5–10, published by Churchill Livingston.

Nashold: Long–term Pain Control by Direct Peripheral–Nerve Stimulation in The Journal of Bone & Joint Surgery, 64: pp. 1–10 (1982).

Racz: Peripheral Nerve Stimulator Implant for Treatment of Causalgia in Stanton–Hicks (ed.); Reflex Sympathetic Dystrophy and Related Syndromes, Kluwer Academic Publishers (1988).

Picaza: Pain Suppression by Peripheral Nerve Stimulation in Surg. Neurol., vol. 4, pp. 115–126 (Jul. 1975).

Law: Retrospective Analysis of 22 Patients with Chronic Pain Treated by Peripheral Nerve Stimulation, in J. Neurosurg., vol. 52, pp. 482–485 (Apr. 1980).

Waisbrod: Direct Nerve Stimulation for Painful Peripheral Neuropathies in The Journal of Bone and Joint Surgery, pp. 470–472 (1985).

Cooney: Chronic Pain Treatment With Direct Electrical Nerve Stimulation in Operative Nerve Repair and Reconstruction, pp. 1551–1561 (1991).

Hassenbush: Long–Term Results of Peripheral Nerve Stimulation for Reflex Sympathetic Dystrophy in J. Neurosurg., vol. 84, pp. 415–423 (1996).

(Continued)

*Primary Examiner*—Jeffrey R. Jastrzab

(57) ABSTRACT

A method for treating pain by subcutaneous electrical stimulation of a peripheral nerve is disclosed. A lead is placed subcutaneously over a peripheral nerve that is causing pain. The peripheral nerve is electrically stimulated to cause paresthesia. The method encompasses subcutaneous placement of an electrical lead near any peripheral nerve causing pain and subsequent electrical stimulation of the nerve to cause paresthesia. In particular, a method for treating intractable occipital neuralgia using percutaneous peripheral nerve electrostimulation techniques is disclosed.

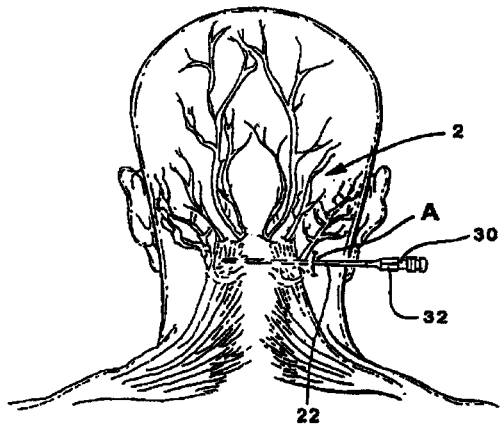

OTHER PUBLICATIONS

Shetter: Peripheral Nerve Stimulation in Neurosurgical Management of Pain; Springer–Verlag, pp. 261–270 (1997).

Racz: Peripheral Stimulator Implant for Treatment of Causalgia Caused by Electrical Burns; Tex Med.; vol. 84; Nov. 1988.

* cited by examiner

EX PARTE REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

ONLY THOSE PARAGRAPHS OF THE SPECIFICATION AFFECTED BY AMENDMENT ARE PRINTED HEREIN.

Column 4, lines 28-38:

The first step of the test implantation and screening stage is the implantation of a screening lead 10. The method involves subcutaneous placement of a screening lead 10 *superior to the fascia 34 or* in the fascia 34 above (superior to) the occipital nerve causing pain and proximal to the level of detected pain. The first step in locating the area to implant the screening lead 10 is to palpate the area of pain to identify the specific nerve that is causing the pain. If it is confirmed that an occipital nerve is causing the pain and the specific occipital nerve has been identified, an introducer needle 22 is used to place the screening lead 10.

Column 4, lines 48-62:

The introducer needle 22 is then subcutaneously placed *superior to the fascia 34 or* in the fascia 34 above (superior to) the nerve 36 that is causing the pain. In the case of treating occipital neuralgia, the introducer needle 22 is placed *superior to the fascia 34 or* in the fascia 34 above (superior to) the occipital nerve that is causing the pain. Fascia 34 is a sheet of fibrous tissue that envelops the body under the skin and also encloses the muscles. In the described method, the introducer needle 22 will be introduced *superior to the fascia 34 or* into the fascia 34 so that the introducer needle will be between the patient's skin and muscle. The nerve causing the pain will be located within or under the musculature. In the case of treating occipital neuralgia, the introducer needle 22 will be introduced *superior to the fascia 34 or* in the fascia 34 so that the introducer needle will be between the patient's skin and the occipital nerve.

AS A RESULT OF REEXAMINATION, IT HAS BEEN DETERMINED THAT:

Claims 1, 14, 15, 17-19, 26, 31, 37 and 43 are determined to be patentable as amended.

Claims 2-13, 16, 20-25, 27-30, 32-36, 38-42 and 44-48, dependent on an amended claim, are determined to be patentable.

1. A method of stimulating a peripheral nerve to treat pain emanating from the peripheral nerve, the method comprising the steps of:
placing a lead having *one or more electrodes all of which are superior to and near the peripheral nerve that is causing pain and* at least one electrode *is* in *and surrounded by* fascia superior to and near the peripheral nerve that is causing pain so that *the* at least one electrode is in the fascia; and
electrically stimulating the peripheral nerve with the at least one electrode in the fascia to cause paresthesia of the painful area.

14. The method of claim 13 wherein the steps of performing test electrical stimulation with the lead includes the step of electrically stimulating the patient by the lead and [screener] *screening* device and evaluating the lead position from the patient's response to the step of electrically stimulating the patient.

15. The method of claim 13 wherein the step of performing test electrical stimulation with the lead includes the step of electrically stimualting the patient by the lead and [screener] *screening* device and developing optimal stimulation parameters based on the patient's response to the step of electrically stimulating the patient.

17. The method of claim [13] *1* wherein [the step of performing test electrical simulation with the lead includes] the step of electrically stimulating the patient *comprises electrically stimulating the patient* with an electrical signal having an amplitude between about 0.5 to about 4.0 volts.

18. The method of claim [13] *1* wherein [the step of performing test electrical stimulation with the lead includes] the step of electrically stimulating the patient *comprises electrically stimulating the patient* with an electrical signal having a rate between about 50 Hz. to about 400 Hz.

19. The method of claim [13] *1* wherein the step of electrically stimulating the patient [with an electrical signal having a rate between about 50 Hz. to about 400 Hz. includes the step of] *comprises* electrically stimulating the patient with an electrical signal having a pulse width between about 90 μsec to about 200 μsec.

26. A method of stimulating an occipital nerve to treat occipital neuralgia comprising the steps of:
placing a lead having *one or more electrodes all of which are superior to and near the occipital nerve that is causing pain and* at least one electrode *is* in *and surrounded by* fascia superior to and near the occipital nerve that is causing pain so that *the* at least one electrode is in the fascia;
electrically stimulating the occipital nerve with the at least one electrode in the fascia to cause paresthesia of the painful area.

31. A method of stimulating a peripheral nerve to treat pain emanating from the peripheral nerve, the peripheral nerve chosen from a group consisting of a supraorbital nerve, a clunial nerve, an iliolinguinal nerve, a median nerve, an ulnar nerve and a sciatic nerve, the method comprising the steps of:
placing a lead having *one or more electrodes all of which are superior to and near the peripheral nerve that is causing pain and* at least one electrode *is* in *and surrounded by* fascia superior to and near the peripheral nerve that is causing pain so that *the* at least one electrode is in the fascia; and
electrically stimulating the peripheral nerve with the at least one electrode in the fascia to cause paresthesia of the painful area.

37. A method of stimulating a peripheral nerve to treat neuralgias emanating from the peripheral nerve, the method comprising the steps of:
placing a lead having *one or more electrodes all of which are superior to and near the peripheral nerve that is causing neuralgia and* at least one electrode *is* in *and surrounded by* fascia superior to and near the peripheral nerve that is causing the neuralgia emanating from the peripheral nerve so that *the* at least one electrode is in the fascia; and
electrically stimulating the peripheral nerve with the at least one electrode in the fascia to cause paresthesia of the area producing the neuralgia.

43. A method of stimulating a peripheral nerve to treat neuralgias emanating from the peripheral nerve, the neuralgias chosen from a group consisting of post herpetic neuralgia, chronic deafferentation pain, chronic peripheral nerve pain, post craniotomy pain, incisional pain, clunial nerve pain, post herniorrhapy pain, localized low back or other spine pain, incisional neuroma pain, stump neuroma pain, incisional scar pain, deafferention pain, chronic peripheral nerve pain, sciatic neuralgia, medial neuralgia and ulnar neuralgia, the method comprising the steps of:

placing a lead having *one or more electrodes all of which are superior to and near the peripheral nerve that is causing neuralgia and* at least one electrode *is* in *and surrounded by* fascia superior to and near the peripheral nerve that is causing the neuralgia emanating from the peripheral nerve so that *the* at least one electrode is in the fascia; and electrically stimulating the peripheral nerve with the at least one electrode in the fascia to cause paresthesia of the area producing the neuralgia.

* * * * *